United States Patent [19]

Adams et al.

[11] Patent Number: 5,502,036
[45] Date of Patent: Mar. 26, 1996

[54] ANTIHERPES PENTAPEPTIDE DERIVATIVES HAVING A SUBSTITUTED ASPARTIC ACID SIDE CHAIN

[75] Inventors: Julian Adams, Ridgefield, Conn.; Pierre L. Beaulieu, Montreal, Canada; Robert Déziel, Ville Mont-Royal, Canada; John DiMaio, Montreal, Canada; Louis Grenier, Laval, Canada; Pierre Lavallée, Rosemere, Canada; Neil Moss, Laval, Canada

[73] Assignee: BioMega Boehringer Ingelheim Research Inc., Laval, Canada

[21] Appl. No.: 208,168

[22] Filed: Mar. 9, 1994

Related U.S. Application Data

[63] Continuation of Ser. No. 927,694, Aug. 7, 1992, abandoned, which is a continuation of Ser. No. 547,670, Jul. 3, 1990, abandoned.

[30] Foreign Application Priority Data

Jul. 7, 1989 [CA] Canada ..................................... 605091

[51] Int. Cl.$^6$ ..................................................... C07K 7/02
[52] U.S. Cl. ................. 514/17; 514/15; 514/16; 514/18; 530/329; 530/330
[58] Field of Search ....................... 514/15–18; 530/329, 530/330

[56] References Cited

U.S. PATENT DOCUMENTS

| | | | |
|---|---|---|---|
| 4,795,740 | 1/1989 | Cohen | 514/14 |
| 4,814,432 | 3/1989 | Freidinger | 530/329 |

OTHER PUBLICATIONS

Bodansky, Principles of Peptide Synth pp. 121, 149–150, 175 (1984).

*Primary Examiner*—Jill Warden
*Assistant Examiner*—David Lukton
*Attorney, Agent, or Firm*—R. P. Raymond; M-E. M. Devlin; A. R. Stempel

[57] ABSTRACT

Disclosed herein are pentapeptide derivatives of the formula X—$NR^1$—CH($R^2$)—C(W)—NH—$CR^3$($R^4$)—C($W^2$)—$NR^5$—CH[$CH_2$C(O)—Y]—C($W^3$)—NH—$CR^6$—[$CR^7$($R^8$)—COOH]—C($W^4$)—NH—$CR^9$($R^{10}$)—Z wherein X is a terminal group, for example, alkanoyl or phenylalkanoyl radicals, $R^1$ is hydrogen, alkyl or phenylalkyl, $R^2$, $R^4$ and $R^{10}$ are selected from amino acid or derived amino acid residues, $R^3$, $R^5$, $R^6$, $R^7$, $R^8$ and $R^9$ are hydrogen or alkyl or $R^7$ and $R^8$ are joined to form a cycloalkyl, $W^1$, $W^2$, $W^3$ and $W^4$ are oxo or thioxo, Y is, for example, an alkoxy or a mono or disubstituted amino, and Z is a terminal group, for example, COOH or $CH_2OH$. The derivatives are useful for treating herpes infections.

7 Claims, No Drawings

ANTIHERPES PENTAPEPTIDE DERIVATIVES HAVING A SUBSTITUTED ASPARTIC ACID SIDE CHAIN

This is a continuation, of application Ser. No. 07/927,694, filed Aug. 7, 1992 (abandoned), which is a continuation of application Ser. No. 07/547,670 filed Jul. 3, 1990 (abandoned).

FIELD OF THE INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to a method of using the peptides to treat herpes infections.

BACKGROUND OF THE INVENTION

The family of herpes viruses is responsible for a wide range of infections that afflict humans and many important domestic animals. The diseases caused by these viruses range from bothersome cold sores to highly destructive infections of the central nervous system (encephalitis). The more common members of this family include herpes simplex virus (types 1 and 2) responsible for cold sores and genital lesions; varicella zoster virus which causes chicken pox and shingles; and Epstein-Barr virus which causes infectious mononucleosis. Although some significant advances have been made in the last decade in antiviral therapy, the need for effective, safe therapeutic agents for treating herpes viral infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The relatively selective action of these peptides against herpes viruses, combined with a wide margin of safety, renders the peptides as desirable agents for combating herpes infections.

The association of peptides with anti-herpes activity is uncommon. Instances of reports of such an association include B. M. Dutia et al., Nature, 321, 439 (1986), E. A. Cohen et al., Nature, 321, 441 (1986), J. H. Subak-Sharpe et al., UK patent application 2185024, published Jul. 8, 1987, E. A. Cohen et al., European patent application 246630, published Nov. 25, 1987, R. Freidinger et al., European patent application 292255, published Nov. 23, 1988, and R. Freiclinger et al., U.S. Pat. No. 4,814,432, issued Mar. 21, 1989. The subject peptides of the previous reports can be distinguished from the peptides of the present application by characteristic structural and biological differences.

SUMMARY OF THE INVENTION

The peptides of this invention are represented by formula 1

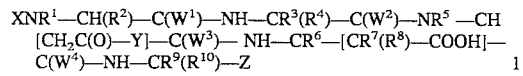

wherein

X is (1–10C)alkanoyl, (1–10C)alkoxycarbonyl, benzoyl, benzoyl monosubstituted or disubstituted with a substituent selected from halo, hydroxy, lower alkyl, lower alkoxy, phenyl, 2-carboxyphenyl or benzyl, 2,2-diphenylacetyl, phenyl(1–10C)alkanoyl or phenyl(1–10C)alkanoyl monosubstituted or disubstituted on the aromatic portion thereof with a substituent selected from halo, hydroxy, lower alkyl, lower alkoxy or phenyl;

$R^1$ is hydrogen, lower alkyl or phenyl(lower)alkyl;

$R^2$ is lower alkyl, hydroxy(lower)alkyl or mercapto(lower)alkyl;

$R^3$, $R^5$, $R^6$ and $R^9$ each independently is hydrogen or lower alkyl;

$R^4$ is hydrogen, lower alkyl, hydroxy(lower)alkyl, mercapto(lower)alkyl, methoxy(lower)alkyl, methylthio(lower)alkyl, lower cycloalkyl or (lower cycloalkyl)methyl;

$R^7$ and $R^8$ each independently is hydrogen or lower alkyl, or $R^7$ and $R^8$ together with the carbon atom to which they are attached form a lower cycloalkyl;

$R^{10}$ is lower alkyl, lower alkenyl or (lower cycloalkyl)-(lower alkyl);

$W^1$, $W^2$, $W^3$ and $W^4$ each independently is oxo or thioxo;

Y is
  a. (1–14C)alkoxy, (3–14C)alkenyloxy, $CH_3(OCH_2CH_2)_n$—O wherein n is the integer 1, 2 or 3, lower cycloalkyloxy, lower alkoxy monosubstituted with a lower cycloalkyl, phenoxy, phenoxy monosubstituted with hydroxy, halo, lower alkyl or lower alkoxy, phenyl(lower)alkoxy or phenyl(lower)alkoxy in which the aromatic portion thereof is substituted with hydroxy, halo, lower alkyl or lower alkoxy, or
  b. $NR^{11}R^{12}$ wherein $R^{11}$ is lower alkyl and $R^{12}$ is lower alkoxy, or
  c. $NR^{11}R^{12}$ a wherein $R^{11}$ is hydrogen or lower alkyl and $R^{12}$ is (1–14C)alkyl, lower cycloalkyl, lower alkyl monosubstituted with a lower cycloalkyl; phenyl, phenyl monosubstituted with halo, lower alkyl or lower alkoxy; phenyl(lower)alkyl, phenyl(lower)alkyl in which the aromatic portion thereof is substituted with halo, lower alkyl or lower alkoxy; or (Het)-lower alkyl wherein Het represents a five or six membered heterocyclic radical containing one or two heteroatoms selected from nitrogen, oxygen or sulfur, or
  d. $NR^{11}R^{12}$ wherein $R^{11}$ and $R^{12}$ together with the nitrogen to which they are attached form a pyrrolidino, piperidino, morpholino, thiomorpholino, piperazino or 4-(lower alkyl) piperazino; and Z is hydrogen; COOH; $CH_2COOH$; $CH_2OH$; 5–1H-tetrazolyl; $COOR^{13}$ wherein $R^{13}$ is lower alkyl; $CONR^{14}R^{15}$ wherein $R^{14}$ and $R^{15}$ each independently is hydrogen or lower alkyl; or $CON(R^{16})OH$ wherein $R^{16}$ is hydrogen or lower alkyl; or a therapeutically acceptable salt thereof.

A preferred group of the peptides of this invention is represented by formula 1 wherein X is (1–10C)alkanoyl; (1–10C)alkoxycarbonyl; benzoyl; benzoyl monosubstituted with halo, hydroxy, lower alkyl, lower alkoxy, phenyl, 2-carboxyphenyl or benzyl; phenyl(1–10C)alkanoyl or phenyl(1–10C)alkanoyl monosubstituted or disubstituted on the aromatic portion thereof with a substituent selected from halo, hydroxy, lower alkyl, lower alkoxy or phenyl; $R^1$ to $R^{10}$, inclusive, and $W^1$ to $W^4$, inclusive, are as defined hereinabove; Y is (1–14C)alkoxy, (3–14C)alkenyloxy, CH₃(OCH₂-CH₂)₃—O, lower cycloalkyloxy, lower cycloalkylmethoxy, phenyl(lower)alkoxy, NR¹¹R¹² wherein R¹¹ is lower alkyl and R¹² is lower alkoxy, or NR¹¹R¹² wherein R¹¹ is hydrogen or lower alkyl and R¹² is (1–14C)alkyl, lower cycloalkyl, lower cycloalkylmethyl, phenyl, phenyl monosubstituted with halo, lower alkyl or lower alkoxy, phenyl(lower)alkyl, phenyl(lower)alkyl monosubstituted with halo, lower alkyl or lower alkoxy, (Het)-lower alkyl wherein Het is a heterocyclic radical selected from 2-pyrrolyl, 2-pyridinyl, 4-pyridinyl, 2-furyl, 2-isoxazolyl and 2-thiazolyl, or NR¹¹R¹² wherein R¹¹ and R¹² together with the nitrogen atom to which they are attached form a pyrrolidino, piperidino or morpholino; and Z is as defined hereinabove; or a therapeutically acceptable salt thereof.

A more preferred group of the peptides is represented by formula 1 wherein X, R⁷, R⁸ and R¹⁰ are as defined hereinabove; R¹ is lower alkyl; R² is lower alkyl or hydroxy-(lower)alkyl; R³, R⁵, R⁶ and R⁹ each independently is hydrogen or methyl; R⁴ is hydrogen, lower alkyl, hydroxy-(lower)-alkyl, methoxy(lower)alkyl, lower cycloalkyl or (lowercyclo-alkyl)methyl; W¹, W² and W³ are oxo, W⁴ is oxo or thioxo, Y is (1–14C)alkoxy, (3–14C)alkenyloxy, CH₃(OCH₂CH₂)₃—O, lower cycloalkyloxy, lower cycloalkylmethoxy, phenyl(lower)alkoxy, N(Me)OMe, NR¹¹R¹² wherein R¹¹ is hydrogen or lower alkyl and R¹² is (1–14C)alkyl, lower cycloalkyl, lower cycloalkylmethyl, phenyl, phenyl(lower)alkyl or pyridinyl(lower alkyl), or NR¹¹R¹² wherein R¹¹ and R¹² together with the nitrogen to which they are attached form a pyrrolidino, piperidino or morpholino; and Z is hydrogen, COOH, CH₂COOH, 5–1H-tetrazolyl, CH₂OH, CONR¹⁴R¹⁵ wherein R¹⁴ and R¹⁵ each independently is hydrogen or lower alkyl, or CON(R¹⁶)OH wherein R¹⁶ is hydrogen or lower alkyl; or a therapeutically acceptable salt thereof.

A most preferred group of the peptides is represented by formula 1 wherein X is acetyl, 4-methylpentanoyl, octanoyl, Boc, benzoyl, 2-biphenylylcarbonyl, 2-(2'-carboxy)biphenylylcarbonyl, phenylacetyl, phenylpropionyl, (4-hydroxyphenyl)propionyl or (3,4-dihydroxyphenyl)propionyl; R¹ is methyl; R² is 1-methylethyl, 1-methylpropyl, 1,1-dimethylethyl or 1-hydroxyethyl; R³ is hydrogen or methyl; R⁴ is hydrogen, lower alkyl, hydroxymethyl, 1-hydroxyethyl, 1-methoxyethyl, cyclopentyl or cyclohexylmethyl; R⁵ is hydrogen or methyl; R⁶ is hydrogen; R⁷ and R⁸ each independently is hydrogen, methyl, ethyl or propyl, or R⁷ and R⁸ together with the carbon atom to which they are attached form a lower cycloalkyl; R⁹ is hydrogen or methyl; R¹⁰ is 1-methylpropyl, 2-methylpropyl, 3-methylbutyl, 2,2-dimethylpropyl or 2-cyclohexylethyl; W¹, W² and W³ are oxo; W⁴ is oxo or thioxo; Y is hexyloxy, 1-methylheptyloxy, decyloxy, dodecyloxy, trans-3-heptenyloxy, cis-3-octenyloxy, CH₃(OCH₂CH₂)₃—O, cyclopentyloxy, cyclohexyloxy, cyclohexylmethoxy, phenylpropoxy, N(Me)OMe, ethylamino, phenylamino, phenylethylamino, N-methyl-N-phenylethylamino, 2-pyridinylethyl, N,N-dimethylamino, N,N-diethylamino, N,N-diisopropylamino, N-methyl-N-octylamino, pyrrolidino, piperidino or morpholino; and Z is hydrogen, COOH, CH₂COOH, 5-1H-tetrazolyl, CH₂OH, CONR¹⁴R¹⁵ wherein R¹⁴ and R¹⁵ each independently is hydrogen, methyl, ethyl or propyl, or CON(R¹⁶)OH wherein R¹⁶ is hydrogen or methyl; or a therapeutically acceptable salt thereof.

Included within the scope of this invention is a pharmaceutical composition comprising an anti-herpes virally effective mount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the peptide of formula 1, of a therapeutically acceptable salt thereof.

Another important aspect involves a method of inhibiting the replication of herpes virus by contacting the virus with a herpes vital ribonucleotide reductase inhibiting amount of the peptide of formula 1, or a therapeutically acceptable salt thereof.

Processes for preparing the peptides of formula 1 are described hereinafter.

DETAILS OF THE INVENTION

GENERAL

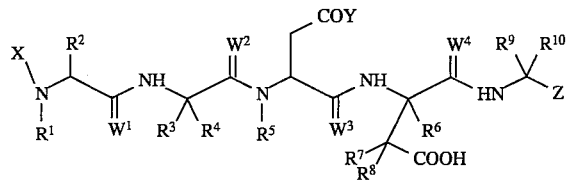

The term 'residue' with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Gly, Vat, Thr, Ala, Ile, Asp, Ser and Leu, represent the residues of glycine, L-valine, L-threonine, L-alanine, L-isoleucine, L-aspartic acid, L-serine and L-leucine, respectively.

The asymmetric carbon atoms residing in the principal linear axis (i.e. the backbone) of the peptides of formula 1, exclusive of the terminal groups, have an S configuration. Asymmetric carbon atoms residing in the side chain of an amino acid or derived amino acid residue, including those in terminal groups, may also have the R configuration. Furthermore, with respect to disubstituted benzoyl and disubstitued phenyl(1–10C)alkanoyl as defined for X of peptides of formula 1, the substituents are selected on the basis that they do not interfere with each others presence.

The term 'halo' as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "lower alkenyl" as used herein means straight chain alkenyl radicals containing two to six carbon atoms and branched chain alkenyl radicals containing three to six carbon atoms and includes vinyl, 1-propenyl, 1-methylethenyl, 2-methyl-1-propenyl, 2-methyl-2-propenyl and 2-butenyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The term "(1–14C)alkyl" as used herein means straight and branched chain alkyl radicals containing from one to fourteen carbon atoms, respectively. The terms "(1–10C)alkoxy" and "(1–14C)alkoxy" as used herein, either alone or in combination with a radical, mean straight and branched chain alkoxy radicals containing from one to ten carbon atoms and one to fourteen carbon atoms, respectively. The term "(3–14C)alkenyloxy" means straight and branched chain alkenyloxy radicals containing from three to fourteen carbon atoms in which the double bond may be cis or trans and is positioned more than one carbon atom away from the oxygen atom of the radical; for example, 3-heptenyloxy and 3-octenyloxy. The term "(1–10C)alkanoyl" as used herein means a straight or branched chain 1-oxoalkyl radical containing from one to ten carbon atoms; for example, acetyl, 4-methyl-1-oxopentyl (or 4-methylpentanoyl) or 1-oxoactyl (or octanoyl). The term "phenyl(1–10)alkanoyl as used herein means phenyl substituted 1-oxoalkyl radicals wherein the 1-oxoalkyl portion thereof is a straight or branched chain 1-oxoalkyl containing from one to ten carbon atoms; for example, 1-oxo-3-phenylpropyl and 1-oxo-5-methyl-6-phenylhexyl.

Additional abbreviations or symbols used hereafter are:

| Boc | 1,1-dimethylethoxycarbonyl or tertiary-butyloxycarbonyl |
| --- | --- |
| DAT | desaminotyrosyl or 1-oxo-3-(4-hydroxyphenyl)propyl |
| Ph | phenyl |
| PhCH$_2$CH$_2$CO | 1-oxo-3-phenylpropyl |
| N—Me—Val | N-methylvalyl residue |
| Tbg | 2(S)-amino-3,3-dimethylbutanoic acid residue |
| N—Me—Tbg | 2(S)-methylamino-3,3-dimethylbutanoic acid residue |
| NMe(octyl) | N-methyl-N-octylamino |
| NMe(decyl) | N-methyl-N-decylamino |
| Asp(cyBu) | (S)-α-amino-1-carboxycyclobutaneacetic acid residue |
| Asp(cyPn) | (S)-α-amino-1-carboxycyclopentaneacetic acid residue |
| Asp(diMe) | 2(S)-amino-3,3-dimethylbutanedioic acid residue |

The symbol "Ψ[CSNH]" used between the three letter representations of two amino acid residues means that the normal amide bond between those residues in the peptide, being represented, has been replaced with a thioamide bond.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of peptide chemistry; for instance, E. Schroder and K. L. Lubke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are thionyl chloride, diphenylphosphoryl azide, 1,1'-carbonyldiimidazole, dicyclohexylcarboliimide, N-hydroxysuccinimide, or 1-hydroxybenzotriazole in the presence of dicyclohexylcarbodiimide. A very practical and useful coupling agent is (benzotriazol-1-yloxy)tris(dimthylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

Process

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schroder and K. Lubke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling in the order of the sequence of the peptide of the amino acid or derived amino acid residues, or fragments of the peptide, which if required are suitably protected, and eliminating all protecting groups, if present, at the completion of the stepwise coupling to obtain the peptide of formula 1. More specific processes are illustrated in the examples hereinafter.

The peptide of formula 1 of this invention can be obtained in the form of a therapeutically acceptable salt.

In the instance where a particular peptide has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phorphoric acid. If desired, a particular acid addition salt is convened into another acid addition salt, such as a non-toxic, pharmaceutically acceptable salt, by treatment with the appropriate ion exchange resin in die manner described by R. A. Boissonnas et al., Helv. Chim. Acta, 43, 1849 (1960).

In the instance where a particular peptide has one or more free carboxy groups, examples of such salts are those with the sodium, potassium or calcium cations, or with strong organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV), Epstein-Barr virus (EBV), equine herpes virus (EHV) and cytomegalovirus.

Noteworthy is the fact that all of the aforementioned viruses are dependent on their own ribonucleotide reductase to synthesize deoxyribonucleotides for their replication. Although this fact may not be directly linked with the antiviral activity found for the present peptides, the latter compounds have been shown so far to have antiviral properties against all viruses dependent on ribonucleotide reductase to synthesis DNA for their replication.

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for example, by using an assay based on genital herpes infection in Swiss Webster mice, described by E. R. Kern, et al., Antiviral Research, 3, 253 (1983).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 10 percent, preferably 0.5 to 5 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantifies of pharmaceutically acceptable salts or of glucose to make the solution isotonic.

Suitable vehicles or carriers for the above noted formulations are described in standard pharmaceutical texts, e.g. in "Remington's Pharmaceutical Sciences", 16th ed, Mack Publishing Company, Easton, Pa., 1980.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or pan of the oral or genital cavity, in an mount sufficient to cover the infected area. The treatment should be repeated, for example, every four to six hours until lesions heal. Healing results usually within 3 to 4 days. No contraindications have been observed.

With reference to systemic administration, the peptide of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of hermetic lesions of the skin. The formulation call be applied nightly to susceptible areas of the skin. Generally, the cosmetic composition contains less of the peptide than corresponding pharmaceutical compositions for topical application. A preferred range of the mount of the peptide in the cosmetic composition is 0.01 to 0.2 percent by weight.

Although the formulation disclosed hereinabove are effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Ascual and F. Rapp in U.S. Pat. No. 4,507,281, Mar. 26, 1985.

The following examples illustrate further this invention. Solution percentages or ratios express volume to volume relationship, unless stated otherwise. Abbreviations used in the examples include Ac: acetyl; Boc: t-butyloxycarbonyl; BOP: Coenzotriazol-1-yloxy)tris(dimethylamino)-phosphonium hexafluorophosphate; Bz1: benzyl; $CH_2Cl_2$: methylenedichloride; DIPEA: diisopropylethylamine; DCC: N,N-dicyclohexylcarbodiimide; DMF: dimethyl formamide; $Et_2O$: diethyl ether;, EtOH: ethanol; HOBt: 1-hydroxybenzotriazole; HPLC: high performance liquid chromatography; i-Pr: 1-methylethyl; MeOH: methanol; TFA: trifluoroacetic acid; THF: tetrahydrofuran. Temperatures are given in degrees centigrade.

EXAMPLE 1

Preparation of the Intermediate BOC-Asp[1(S)-methylheptyloxy]-OH

A solution of Boc-Asp-OBzl (10.2 g, 31.6 mmol) in acetonitrile was added at 0° to a mixture of N,N'-carbonyldiimidazole (5.6g, 34.7 mmol), DIPEA (8 ml, 46 mmol) and 2(S)-octanol (6 ml, 37.9 mmol) and 4-dimethylaminopyridine (200 mg). The mixture was stirred for 3 h and then concentrated to dryness. The residue was dissolved in EtOAc. The solution was washed with 1N aqueous HCl, 1N aqueous $NaHCO_3$, dried ($MgSO_4$) and concentrated. The resultant oil was purified by chromatography ($SiO_2$, eluent: hexane-EtOAc, 7:3) to give Boc-Asp[1(S)-methylheptyloxy]-OBzl. Hydrogenation of the latter compound in the presence of 20% $Pd(OH)_2/C$ in ethanol solution afforded the title compound as a solid.

NMR(200 MHz, $CDCl_3$)δ 0.9(m,3H), 1.25(m,10H), 1.45(s,9H), 2.8(dd, 1H), 3.0(dd, 1H), 4.6(m,1H), 4.95(m, 1H) and 5.55(d,1H).

Analogous esters of Boc-Asp-OH were prepared in the same manner.

EXAMPLE 2

Preparation of the Intermediate Boc-Asp($NEt_2$)-OH

BOP (2.20g, 5.0 mmol) was added under $N_2$ to a cooled (0°) solution of Boc-Asp-OBzl (1.90 g, 4.6 mmol) in $CH_2Cl_2$ (50 ml). After 3 min $NHEt_2$.HCl (0.55 g, 5.0 mmol) and DIPEA (2.4 ml, 1.38 mmol) were added. The resultant solution was stirred at 20°–22° for 18 h. The solution was washed with 10% aqueous citric acid (2 ×), 10% aqueous $NaHCO_3$ (2 ×) and brine (2 ×). The organic layer was dried ($MgSO_4$) and concentrated to give an oil. After $SiO_2$ chromatography of the oil using hexane-EtOAc (7:3) as the eluent, Boc-Asp(NEtz)-OBzl (1.55 g, 89%) was obtained as an oil. Under a $N_2$ atmosphere, a solution of the latter compound (1.55 g, 4.09 mmol) in MeOH (100 ml) was mixed with 5% Pd/C (155 mg). The mixture was shaken on a Parr apparatus under $H_2$ (50 psi) for 90 min. The mixture was filtered through a 45 m membrane and the filtrate concentrated to give Boc7Asp(NEta)-OH (1.15 g, 98%) as an oil. The structure of the product was confirmed by NMR.

In the same manner, corresponding N-substituted asparagine analogs were obtained by replacing $NEHt_2$. HCl with the appropriate amine or amine salt (e.g. pyrrolictine or N,O-dimethyihydroxylamine hydrochloride).

The intermediates of examples 1 and 2 or their analogs can be incorporated into corresponding peptides of formula 1 according to the procedure of example 4.

EXAMPLE 3

Preparation of the Intermediate Boc-Asp(OBzl)Ψ[CSNH]Leu-OBzl

A stirred mixture of Boc-Asp(OBzl)Leu-OBzl (2.90 g, 5.51 mmol) and Lawesson's reagent (1.12 g, 2.7 mmol), see U. Pederson et al., Tetrahedron, 38, 3267 (1982), in toluene (30 ml) was heated at reflux for 2 h. Column chromatography with $SiO_2$(3.5×30 cm) and elution with $CH_2Cl_2$ gave the title compound (2.0 g), MS:543$(M+H)^+$, as a yellow oil (major fraction).

Analogous thioamides can be prepared in the same manner and incorporated into corresponding peptides of formula 1 by the procedure of example 5.

EXAMPLE 4

Preparation of 3-Alkyl- or 3,3-Dialkyl-L-aspartic Acid Intermediates and (S)-α-Amino-1-carboxycycloalkylacetic Acid Intermediates These intermediates, which can be used to prepare peptides of formula 1 in which $R^7$ and $R^8$ are other than hydrogen, can be prepared according to the method of M. Bochenska and J. F. Biernat, Rocz. Chem., 50, 1195 (1976); see Chem. Abstr., 86, 43990r (1977).

More specifically exemplified, (±)-Boc-Asp(cyPn)(OBzl)-OH was prepared as follows: To a solution of 1-bromocyclopentanecarboxylic acid ethyl ester [17.1 g, 77.3 mmol, described by D. N. Harpp et al., J. Org. Chem., 46, 3420 (1975)] and freshly distilled ethyl isocyanoacetate (12.7 g, 122 mmol) in a mixture of dimethylsulfoxide and $Et_2O$ (1:1, 120 ml) was added sodium hydride (4.5 g, 60% dispersion in mineral oil, 122 mmol) in small portions over 5 h. The resulting red slurry was stirred at room temperature for 16 h after which time it was treated with a saturated aqueous solution of ammonium chloride (5 ml). The mixture was diluted with water (500 ml). The resulting mixture was extracted (2×) with ethyl acetate. The ethyl acetate layers were combined and washed with water (2×) and then with brine. Drying ($MgSO_4$), filtering and concentration of the extract afforded a dark red oil. This material was flash chromatographed through a 5×25 cm column of silica gel [eluent: ethyl acetate-hexane (1:10)]. Concentration of the appropriate fractions provided αcyano-1-carboxycyclopentaneacetic acid diethyl ester as a clear colorless viscous liquid (13 g, 66 %).

The latter compound (13 g, 51 mmol) was mixed with 6N aqueous HCl (60 ml) at 0° . After dissolution, the reaction mixture was heated in a oil bath at 120° for 24 h. After this time water was removed from the mixture using a dry ice rotory evaporator. The resulting white solid was dried under high vacuum for 18 h. The dried material was dissolved in a mixture of dioxane (50 ml) and 3N aqueous NaOH (52 ml). A solution of di(tertiarybutyl) dicarbonate (14.6 g, 67 mmol) in dioxane (25 ml) was added to the solution. The mixture was stirred at room temperature for 16 h. Additional 3N aqueous NaOH was added at intervals insuring a pH of about 10. The mixture was diluted with water (500 ml) and extracted (2×) with $Et_2O$ (200 ml). The aqueous phase was rendered acidic (pH=3) with solid citric acid and extracted (2×) with ethyl acetate (300 ml). The combined ethyl acetate extracts were washed with water (3×) and brine. Drying, filtering and concentration of the extract afforded Boc-Asp(cyPn)-OH as a white solid (14 g, 96%).

To a solution of the latter compound (7.2 g, 25 mmol) in dry DMF (50 ml) was added $K_2CO_3$ (7.6 g, 55 mmol) and benzyl bromide (6.6 ml, 55 mmol). The reaction mixture was stirred at room temperature for about 7 h. Thereafter, the reaction mixture was poured into a mixture of water (500 ml) and ethyl acetate (350 ml). The organic phase was washed with water (2×) and brine. Drying, filtering and concentration of the extract provided a pale yellow viscous liquid. This material was flash chromatographed through a 5×20 cm column of silica gel, eluting with hexane-ethyl acetate (12:1). Concentration of the appropriate fractions provided the dibenzyl derivative of Boc-Asp-(cyPn)-OH as a low melting white solid (11 g, 94%). The dibenzyl product was dissolved in THF (100 ml) and an aqueous solution of LiOH (23.5 ml, 1N) was added. After 4 h, the reaction mixture was poured into water and extracted (3×) with EtaO. The aqueous phase was rendered acidic with 10% aqueous citric acid and extracted (2×) with ethyl acetate. The ethyl acetate layers were combined, dried (MgSO$_4$), filtered and concentrated to provide Boc-Asp(cyPn)(OBzl)-OH as a clear color less gum (7.3 g, 82%).

EXAMPLE 5

General Procedure for the Solid Phase Preparation of Peptides of Formula 1

A modified version of the solid phase method of R. B. Merrifield, J. Am. Chem. Soc., 85, 2149 (1963) was used to prepare the peptides preferably using a BHA-photoresin such as [4-(2chloropropionyl)phenoxy]acetamidomethyl-copoly(styrene- 1% divinyl-benzene) resin, see D. Bellof and M. Mutter, Chemia, 39, 317 (1985). Protection of free carboxy groups and hydroxy groups was provided by the Bzl protective group. Typically, a Boc-amino acid, representing the C-terminal unit of the desired peptide, e.g. Boc-Leu-OH, was linked to the above noted BHA-photoresin by the potassium fluoride method of K. Horiki et al., Chem. Lett., 165 (1978), using 9 molar equivalents of KF and 3.6 molar equivalents of Boc-Leu-OH, for example in DMF at 70° C. for 24 hours, to give [4-{2-(Boc-leucyl }propionyl }phenoxy]acetamidomethyl-copoly(styrene-1% divinylbenzene) resin. The dried amino acid-solid support typically showed a leucine content of 0.6 to 0.8 mmol/g for the product, as determined by deprotection of an aliquot, followed by picric acid titration, B. F. Gisin, Anal. Chim. Acta, 58, 248 (1972). The latter amino acid-solid support was used to build up the required sequence of units (i.e. amino acid residues, derived amino acid residues) of the desired peptide by solid phase methodology. Two molar equivalents (per mole of the amino-acid solid support) of the appropriate amino acid residues were coupled serially to the solid support system using BOP (2 molar equivalents), or BOP (2 molar equivalents)/HOBt (1 molar equivalent), in the presence of N-methyl-morpholine (6 molar equivalents) in dry DMF. Completion of coupling was verified by a negative ninhydrin test, E. Kaiser et al., Anal Biochem., 34, 595 (1979). Double coupling was used when necessary.

Cleavage of the protected peptide from the solid support was accomplished by irradiation at 330 nm in EtOH/DMF (1:4) at 0° under an argon atmosphere for 6 to 18 h. Protective groups (Bzl), if present, were removed from the cleavage product by hydrogenolysis over 5% or 10% Pd/C or 20% Pd(OH)$_2$/C by standard procedures (cf. example 1). Purification of the final product was performed by reversed-phase HPLC to better than 95% homogeneity using 0.06% aqueous TFA/acetonitrile gradients.

More specifically exemplified, the protected peptide, DAT-N-Me-Val-Ile-Asp(NEt$_2$)-Asp(OBzl)-Leu-OH was assembled by the preceding procedure on a BHA photoresin using BOP/HOBt as the coupling agent, followed by cleavage of the resulting protected peptide resin by photolysis under argon at −5° for 6 h. DMF:EtOH (4:1) was used as the photolysis medium. Deprotection of the cleavage product was effected by hydrogenolysis using 5% Pd/C as catalyst. Purification of the product was done by HPLC, the product being dissolved in 0.1N aqueous NH$_4$OH solution and the solution adjusted to pH$_6$ with 0.1N aqueous AcOH. Whatman Partisil® 100DS-3 C-18 column (2.2×50 cm$^2$), 10 micron particle size, was used. Elution was done with a gradient of acetonitrile and 0.06% aqueous TFA. Pure fractions (determined by analytical HPLC) were pooled and lyophilized to give DAT-N-Me-Val-Ile-Asp(NEt$_2$)-Asp-Leu-OH. MS: 791 (M+H)$^+$.

EXAMPLE 6

Preparation of PhCH$_2$CH$_2$CO-N-Me-Val-Ile-Asp(pyrrolidino)-AspΨ-[CSNH]Leu-OH (Example of a solution phase procedure for preparing the peptides of formula 1)

A solution of the title compound of example 3 (500 mg, 0.93 mmol) in 50% TFA in CH$_2$Cl$_2$ (20 ml) was stirred at 0 for 30 min. Solvent was removed from the mixture under reduced pressure. Portions of MeOH and benzene were added separately to the residue and evaporated in turn to remove residual TFA. In this manner, H-Asp(OBzl)Ψ[CSNH]Leu-OBzl.TFA was obtained as a yellow oil. The latter compound (500 mg, 0.93 mmol) was dissolved in DMF (5 ml). DIEA was added to the solution to adjust the pH to 7.5. Boc-Asp(pyrrolidino)-OH (286 mg, 1 mmol) was added to the solution, followed by BOP (429 mg, 1 mmol) and enough DIEA to readjust the mixture to pH 7.5. The reaction mixture was stirred for 2 h at room temperature then poured into ice water (75 ml). The aqueous mixture was extracted with ethyl acetate. The extract was washed with water and brine, dried (MgSO$_4$) and evaporated. A solution of the residue was filtered through a short column of SiO$_2$. Evaporation of the eluent gave Boc-Asp(pyrrolidino)-Asp(OBzl)Ψ[CSNH]Leu-OBzl.

Repetition of the deprotection and coupling steps of the last paragraph, using serially Boc-Ile-OH, Boc-N-Me-Val-OH and PhCH$_2$CH$_2$COOH, in place of Boc-Asp(pyrrolidino)-OH, yielded the protected form (two Bzl groups) of title compound (390 mg). The latter compound was aleprotected as follows: Hydrogen fluoride (10 ml) was distilled into a reaction flask containing the compound (260 mg) and d,l-methionine (1.0 g). The mixture was stirred at −20C. for 30 min, then at 0 for 30 min. The hydrogen fluoride was evaporated. The residue was triturated with Et$_2$O. The solid was collected on a filter and washed with 20% aqueous AcOH. Preparative HPLC (Waters Delta Prep 3000®, Millipore Corporation, Milford, Mass., USA; injection (1.1 g of the solid in 20% aqueous HOAc, flow: 100% H$_2$O) gave the title compound MS: 789 (M+H)$^+$.

The procedures of examples 5 or 6 were used to prepare the peptides listed in the tables of example 7, with modifications noted therein in some instances. Commercially available Boc-amino acids were used. Unnatural amino acids were used in their Boc protected form; they were either commercially available, readily prepared from commercially available corresponding amino acids by reaction with di-tertiary-butyl carbonate, or prepared by standard methods.

Note that N-alkylated Boc amino acids are commercially available, e.g. Boc-N-methylvaline, or they can be prepared by standard N-alkylation of corresponding Boc-amino acids. For example, Boc-N-Me-Asp(NEt$_2$)-OH was obtained by reacting Boc-Asp(NEt$_2$)-OH with 2.5 molar equivalents of methyl iodide and 2.1 molar equivalents of potassium hydride in THF at 0C. for 18 h to give a mixture of Boc-N-Me-Asp(NEt$_2$)-OH and its corresponding methyl ester. The mixture was esterified fully (diazomethane) and then saponified (NaOH/H$_2$O/dioxane) to yield the desired compound.

EXAMPLE 7

Inhibition of Herpes Simplex Virus (HSV, type 1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay and Results for Exemplified Peptides

By following the procedure described by P. Gaudreau et al., J. Biol. Chem., 262, 12413 (1987), the assay results listed in following tables 1 to 5 were obtained. The assay result for each peptide is expressed as the concentration of the peptide producing 50% of the maximal inhibition (IC$_{50}$) of enzyme activity. The number of units of the enzyme preparation used in each assay was constant, based on the specific activity of the enzyme preparation. The results are relative to the activity obtained in control experiments without peptide and represent the mean of four assays that varied less than 10% with each other.

TABLE 1

PhCH$_2$CH$_2$CO—N—Me—Val—Ile—NH—CH(CH$_2$COY)—CO—Asp—Leu—OH (Peptide of Formula 1: X = .PhCH$_2$CH$_2$CO, R$^1$ = CH$_3$, R$^2$ = CH(CH$_3$)$_2$, R$^3$, R$^5$, R$^6$, R$^7$, R$^8$ and R$^9$ = H, R$^4$ = CH(CH$_3$)C$_2$H$_5$, R$^{10}$ = CH$_2$CH(CH$_3$)$_2$, W$^1$, W$^2$, W$^3$ and W$^4$ = O, Y is as shown below and Z = COOH)

| Entry No. | Y | FAB/MS (M + H)$^+$ | IC$_{50}$ (μM) |
|---|---|---|---|
| 1 | 1(S)-methylheptyloxy | 832 | 0.7 |
| 2 | 1(R)-methylheptyloxy | 832 | 0.7 |
| 3 | NMe$_2$ | 747 | 0.19 |
| 4 | NEt$_2$ | 775 | 0.26 |
| 5 | N(i-Pr)$_2$ | 802 | 0.25 |
| 6 | pyrrolidino | 773 | 0.11 |
| 7 | morpholino | 789 | 0.18 |
| 8 | N(Me)OMe | 762 | 0.19 |

TABLE 2

X = DAT—N—Me—Val—Ile—NH—CH(CH$_2$COY)—CO—Asp—Leu—OH (Peptides of formula 1: X = DAT, R$^1$ = CH$_3$, R$^2$ = CH(CH$_3$)$_2$, R$^3$, R$^5$, R$^6$, R$^7$, R$^8$ and R$^9$ = H, R$^4$ = CH(CH$_3$)C$_2$H$_5$, R$^{10}$ = CH$_2$CH(CH$_3$)$_2$, W$^1$, W$^2$, W$^3$ and W$^4$ = O, Y is as shown below and Z = COOH)

| Entry No. | Y | FAB/MS (M + H)$^+$, (M + Na)$^+$ | IC$_{50}$ (μM) |
|---|---|---|---|
| 9 | OCH$_2$CH$_2$CH$_2$Ph | 854 | 0.65 |
| 10 | NHPh | 811,833 | 1.6 |
| 11 | NHCH$_2$CH$_2$Ph | 839 | 0.51 |
| 12 | NMe$_2$ | 763 | 0.09 |
| 13 | NEt$_2$ | 791 | 0.27 |
| 14 | NMeCH$_2$CH$_2$Ph | 853 | 0.38 |
| 15 | NMeCH$_2$CH$_{2(2\text{-pyridyl})}$ | 854 | 0.29 |
| 16 | morpholino | 805 | 0.37 |

TABLE 3

DAT—Val—Ile—NH—CH(CH$_2$COY)—CO—Asp—Leu—OH (Peptides of formula 1: X = DAT, R$^1$, R$^3$, R$^5$, R$^6$, R$^7$, R$^8$ and R$^9$ = H, R$^2$ = CH(CH$_3$)$_2$, R$^4$ = CH(CH$_3$)C$_2$H$_5$, R$^{10}$ = CH$_2$CH(CH$_3$)$_2$, W$^1$, W$^2$, W$^3$ and W$^4$ = O, Y is as shown below and Z = COOH)

| Entry No. | Y | FAB/MS (M + H)$^+$,(M + Na)$^+$ | IC$_{50}$ (μM) |
|---|---|---|---|
| 17 | NHCH$_2$CH$_2$Ph | 825,847 | 1.7 |
| 18 | NHCH$_2$CH$_3$ | 749 | 1.75 |
| 19 | NEt$_2$ | 777 | 0.56 |
| 20 | NMeCH$_2$CH$_2$Ph | 839 | 0.55 |

TABLE 4

| Entry No. | Peptide | FAB/MS (M + H)$^+$ | IC$_{50}$ (μM) |
|---|---|---|---|
| 21 | 2-Biphenylylcarbonyl-Val—Ile—Asp—(NHCH$_2$CH$_2$Ph)—Asp—Leu—OH | 857 | 1.25 |
| 22 | Benzoyl-Val—Ile—Asp—(NHCH$_2$CH$_2$Ph)—Asp—Leu—OH | 781 | 7.6 |
| 23 | Ac—Val—Ile—Asp(NHCH$_2$CH$_2$Ph)—Asp—Leu—OH | 719 | 18 |
| 24 | Boc—N—Me—Val—Ile—Asp(NHCH$_2$CH$_2$Ph)—Asp—Leu—OH | 805 | 1.6 |
| 25 | 4-Methylpentanoyl-N—Me—Val—Ile—Asp(NEt$_2$)—Asp—Leu—OH | 741 | 0.5 |
| 26 | PhCH$_2$CH$_2$CO—N—Me—Val—Thr—Asp(NEt$_2$)—Asp—Leu—OH | 763 | 0.3 |
| 27 | PhCH$_2$CH$_2$CO—N—Me—Val—Ile—Asp(morpholino)-Asp—Leu—NEt$_2$ | 844 | 2.6 |
| 28 | (3,4-Dihydroxy-Ph)—CH$_2$CH$_2$CO—N—Me—Val—Ile—Asp(pyrrolidino)-Asp—Leu—OH | 804 | 0.25 |

TABLE 5

| Entry No. | Peptide | FAB/MS (M + Na)$^+$ | IC$_{50}$ (μM) |
|---|---|---|---|
| 29 | PhCH$_2$CH$_2$CO—N—Me—Val—Ile—Asp(dodecyloxy)-Asp—Leu—OH | 910 | 4.2 |
| 30 | 4-Methylpentanoyl-N—Me—Val—Ile—Asp[1(S)-methylheptyloxy]-Asp—Leu—OH | 820 | 1.7 |
| 31 | PhCH$_2$CH$_2$CO—N—Me—Val—Ile—Asp[1(S)-methylheptyloxy]-Asp—Leu—NH$_2$ | 831 | 1.9 |
| 32 | PhCH$_2$CH$_2$CO—N—Me—Val—Ile—Asp[NMe(octyl)]-Asp—Leu—OH | 867 | 0.26 |
| 33 | PhCH$_2$CH$_2$CO—N—Me—Val—Tbg—Asp(pyrrolidino)-Asp(cyBu)-Leu—OH | 835 | 0.06 |
| 34 | PhCH$_2$CH$_2$CO—N—Me—Val—Tbg—Asp[1(S)-methylheptyloxy]-Asp(cyBu)-Leu—OH | 908 | 0.18 |
| 35 | PhCH$_2$CH$_2$CO—N—Me—Val—Ile—Asp(pyrrolidino)- | 802 (M + H)$^+$ | 0.07, 0.28 |

TABLE 5-continued

| Entry No. | Peptide | FAB/MS (M + Na)+ | IC$_{50}$ (μM) |
|---|---|---|---|
|  | Asp(diMe)-Leu—OH (obtained is a diastereoisomeric mixture, separable by HPLC) |  |  |
| 36 | PhCH$_2$CH$_2$CO—N—Me—Val—Ile—Asp(pyrrolidino)-Asp—NHCH$_2$CH$_2$C(CH$_3$)$_3$ | 764 | 0.87 |
| 37 | PhCH$_2$CH$_2$CO—N—Me—Val—Ile—Asp[1(S)-methylheptyloxy]-Asp—Leu—OCH$_3$ | 869 | 2.0 |
| 38 | PhCH$_2$CH$_2$CO—N—Me—Val—Ile—Asp(pyrrolidino)-Asp—NHCH$_2$CH$_2$CH(CH$_3$)$_2$ | 729(M + 1)+ | 1.3 |
| 39 | PhCH$_2$CH$_2$CO—N—Me—Val—Ile—Asp(pyrrolidino)-Asp—NH(3-cyclohexylpropyl) | 806 | 1.8 |
| 40 | PhCH$_2$CH$_2$CO—N—Me—Val—Ile—Asp(pyrrolidino)-Ψ[CSNH]Asp—Leu—OH | 789(M + 1) | 0.16 |
| 41 | PhCH$_2$CH$_2$CO—N—Me—Val—Ile—Asp(pyrrolidino)-Asp—NHCH(CH$_3$)CH$_2$CH(CH$_3$)$_2$ | 743(M + 1)+ | 2.6 |

Other examples of the peptides of formula 1 are:

| 42 | PhCH$_2$CH$_2$CO—N—Me—Val—Ile—Asp(NEt$_2$)—Asp—Leu—NHOH |
| 43 | PhCH$_2$CH$_2$CO—N—Me—Val—Ile—Asp(NEt$_2$)—Asp—Leu—N(Me)OH |
| 44 | PhCH$_2$CH$_2$CO—N—Me—Val—Ile—Asp(NEt$_2$)—Asp—(L-leucinol) |
| 45 | PhCH$_2$CH$_2$CO—N—Me—Val—Ile—Asp(NMe$_2$)—Asp—NHCH[CH$_2$CH—(CH$_3$)$_2$]-5-1H-tetrazole |
| 46 | PhCH$_2$CH$_2$CO—N—Me—Val—Ile—Asp(pyrrolidino)-Asp—NHCH—[CH$_2$CH$_2$CH(CH$_3$)$_2$]COOH |
| 47 | PhCH$_2$CH$_2$CO—N—Me—Val—Ile—Asp(NEt$_2$)—Asp—NHCH[CH$_2$CCH$_3$—(=CH$_2$)]—COOH |
| 48 | PhCH$_2$CH$_2$CO—N—Me—Val—Ile—Asp(pyrrolidino)-Asp—NHCH—[CH$_2$C(CH$_3$)$_3$]—COOH |
| 49 | PhCH$_2$CH$_2$CO—N—Me—Val—Ile—Asp(pyrrolidino)-NHCH[CH(CH$_3$)COOH]—CO—Leu—OH |
| 50 | PhCH$_2$CH$_2$CO—N—Me—Val—Ile—Asp(pyrrolidino)-Asp—NHCH—[CH$_2$CH(CH$_3$)$_2$]CH$_2$COOH |
| 51 | [2-(2'-Carboxy)biphenylyl]carbonyl-N—Me—Val—Ile—Asp(pyrrolidino)-Asp—Leu—OH |
| 52 | PhCH$_2$CH$_2$CO—N—Me—Val—NHCH(cyclohexylmethyl)-CO—Asp—(pyrrolidino)-Asp—Leu—OH |
| 53 | PhCH$_2$CH$_2$CO—N—Me—Val—Ile—Asp(pyrrolidino)-Asp—Leu—NH$_2$ |
| 54 | PhCH$_2$CH$_2$CO—N—Me—Val—Ile—Asp(NHCH$_2$CH$_2$Ph)—Asp—Leu—NH$_2$ |
| 55 | PhCH$_2$CH$_2$CO—N—Me—Tbg—Ile—Asp[NMe(decyl)]-Asp—Leu—OH |
| 56 | PhCH$_2$CH$_2$CO—N—Me—Val—Ile—Asp(morpholino)-Asp—Leu—NEt$_2$ |

Entries No. 42 and No. 43. The corresponding protected C-terminal acid was coupled with hydroxylamine hydrochloride or N-methylhydroxylamine hydrochloride, respectively, using BOP/DIPEA in CH$_2$Cl$_2$, followed by hydrogenation to remove the Bzl on the Asp residue.

Entry No. 45. The tetrazole residue or unit for this peptide was derived from Boc-Leu-NH$_2$ in this manner: Boc-Leu-NH$_2$ was converted to the corresponding nitrile derivative by treatment with p-toluenesulfonyl chloride in CH$_2$Cl$_2$ in the presence of excess pyridine and a catalytic amount of 4-dimethylamino-pyridine (Fieser and Fieser, "Reagents for Organic Synthesis", John Wiley and Sons, Inc., New York, N.Y., USA, 1967, vol 1, p 1183). The nitrile derivative then was mixed with tributyl tin azide, J. G. A. Luijten et al., Rec. Tray., 81,202 (1962), giving a tetrazole tin derivative. [Cf. K. Sisido et al., Journal of Organometallic Chemistry, 33, 337 (1971).] The latter was treated with HCl gas in Et$_2$O to afford the desired tetrazole residue as a hydrochloride salt which was used as such for the coupling with an activated amino acid of the appropriate tetrapeptide intermediate, e.g. PhCH$_2$CH$_2$CO-N-Me-Val-Ile-Asp(NMe$_2$)-Asp(OBzl)-OH, prepared according to the procedure of example 5.

Entry No. 46. The 2(S)-amino-5-methylhexanoic acid methyl ester (Boc-homoleucine methyl ester) employed for the preparation of this peptide was obtained by reacting [(CH$_3$)$_2$CH—CH$_2$]$_2$CuLi, prepared by the method of D. Seebach and H. Neumann, Chem. Ber., 107, 847 (1974), with the O-tosyl derivative of Boc-Ser-OCH$_3$ according to the conditions reported by A. Bernardini et al., Tetrahedron Letters, 24, 3717 (1983); followed by Boc deprotection with TFA/CH$_2$Cl$_2$ of the resulting Boc-2(S)-amino-5-methylhexanoic acid methyl ester. Subsequent coupling of the 2(S)-amino-5-methylhexanoic methyl ester so obtained with PhCH$_2$CH$_2$CO-N-Me-Val-Ile-Asp(pyrrolidino)Asp(OBzl)-OH and deprotection of the coupling product gave the corresponding peptide of formula 1.

Entry No. 47: The 2(S)-amino-4-methyl-5-hexenoic acid methyl ester employed for the preparation of this peptide was obtained by converting Boc-Ser-OH to its corresponding β-lactone by the method of J. C. Vederas et ai., J. Am. Chem. Soc., 107 7105 (1985) and reacting the β-lactone with the organolithium derivative derived from 2-propylene bromide according to the method of D. Seebach and H. Neumann, Chem. Ber., 107, 847 (1974) to give 2(S)-amino-4-methyl-5-hexenoic acid. Subsequent esterification of the latter compound with diazomethane gave the desired corresponding methyl ester.

Entry No. 50. The Boc-3(S)-amino-5-methylhexanoic acid employed in the preparation of this peptide was obtained by an Arndt-Eistert reaction starting from Boc-Leu-OH, W. E. Bachmann and W. S. Struve, Organic Reactions, 1, 38 (1942).

Entries No. 53 and 54. Lucinamide was coupled with the appropriate protected fragment followed by hydrogenolysis to remove the Bzl protecting group. For example, entry no. 53 was obtained by coupling PhCH$_2$CH$_2$CO-N-Me-Val-Ile-Asp-(pyrrolidino)-Asp(Bzl)-OH, prepared according to the procedure of example 5, with leucinamide using BOP in the presence of DIPEA, followed by hydrogenation to remove the Bzl on the Asp residue.

Entry No. 56. The corresponding protected C-terminal acid was coupled with diethylamine hydrochloride using BOP/HOBt in the presence of N-methylmorpholine, followed by hydrogenation to remove the Bzl on the Asp residue.

We claim:

1. A peptide of formula 1

X-NR$^1$-CH(R$^2$)-C(W$^1$)-NH-CR$^3$(R$^4$)-C(W$^2$)-NR$^5$-CH[CH$^2$C(O)-Y]-C(W$^3$)-NH-CR$^6$-[CR$^7$CR$^8$)-COOH]-C(W$^4$)-NH-CR$^9$(R$^{10}$)-Z  1 wherein X is 4-methylpentanoyl, phenylpropionyl, (4-hydroxy-phenyl)propionyl or (3,4-dihydroxyphenyl)propionyl; R$^1$ is methyl; R$^2$ is 1-methylethyl; R$^3$ is hydrogen; R$^4$ is lower alkyl; R$^5$ is hydrogen; R$^6$ is hydrogen; R$^7$ and R$^8$ each independently are hydrogen or R$^7$ and R$^8$ together with the carbon atom to which they are attached form a lower cycloalkyl; R$^9$ is hydrogen or methyl; R$^{10}$ is 2-methylpropyl, 3-methylbutyl; 2,2-dimethylpropyl or 2-cyclohexylethyl; W$^1$, W$^2$ and W$^3$ are oxo; W$^4$ is oxo or thioxo; Y is 1-methylheptyloxy, dodecyloxy, N(Me)OMe, N,N-diethylamino, N,N-diisopropylamino, N-methyl-N-octylamino, pyrrolidino or morpholino; and Z is hydrogen, COOH, CH$_2$OH, CONR$^{14}$R$^{15}$ wherein R$^{14}$ and R$^{15}$ each independently are hydrogen; or a therapeutically acceptable salt.

2. A pharmaceutical composition comprising a peptide as recited in claim 1, or a therapeutically acceptable salt thereof, and a pharmaceutically or veterinarily acceptable carrier.

3. A cosmetic composition comprising a peptide as recited in claim 1, or a therapeutically acceptable salt thereof, and a physiologically acceptable carrier suitable for topical application.

4. A method of treating a herpes viral infection in a mammal comprising administering thereto an effective amount of a peptide as recited in claim 1, or a therapeutically acceptable salt thereof.

5. A method of claim 4 wherein the herpes viral infection is a herpes simplex viral infection.

6. A method of inhibiting the replication of herpes virus comprising contacting the virus with a herpes viral ribonucleotide reductase inhibiting amount of the peptide as recited in claim 1, or a therapeutically acceptable salt thereof.

7. A peptide selected from the group of

DAT-N-Me-Val-Ile-Asp(NEt$_2$)-Asp-Leu-OH

PhCH$_2$CH$_2$CO—N-Me-Val-Ile-Asp[1(S)-methylheptyloxy]-Asp-Leu-OH

PhCH$_2$CH$_2$CO—N-Me-Val-Ile-Asp[1(R)-methylheptyloxy]-Asp-Leu-OH

PhCH$_2$CH$_2$CO—N-Me-Val-Ile-Asp(NEt$_2$)-Asp-Leu-OH

PhCH$_2$CH$_2$CO—N-Me-Val-Ile-Asp[N(i-Pr$_2$)]-Asp-Leu-OH

PhCH$_2$CH$_2$CO—N-Me-Val-Ile-Asp(pyrrolidino)-Asp-Leu-OH

PhCH$_2$CH$_2$CO—N-Me-Val-Ile-Asp(morpholino-Asp-Leu-OH

PhCH$_2$CH$_2$CO—N-Me-Val-Ile-Asp[N(Me)OMe]-Asp-Leu-OH

DAT-N-Me-Val-Ile-Asp[NMeCH$_2$CH$_2$(2-pyridyl)]-Asp-Leu-OH (3,4-dihydroxy-Ph)-CH$_2$CH$_2$CO—N-Me-Val-Ile-Asp(pyrrolidino )-Asp-Leu-OH PhCH$_2$CH$_2$CO—N-Me-Val-Ile-Asp(pyrrolidino)-Asp-NHCH[CH$_2$CH$_2$-CH(CH$_3$)$_2$]—COOH PhCH$_2$CH$_2$CO—N-Me-Val-Ile-Asp(pyrrolidino)-Asp-NHCH[CH$_2$C(CH$_3$)$_2$]—COOH PhCH$_2$CH$_2$CO—N-Me-Val-Ile-Asp(dodecyloxy)-Asp-Leu-OH 4-Methylpentanoyl-N-Me-Val-Ile-Asp[1(S)-methylheptyloxy]-Asp-Leu-OH PhCH$_2$CH$_2$CO—N-Me-Val-Ile-Asp[1(S)-methyl-heptyloxy]-Asp-Leu-NH$_2$ PhCH$_2$CH$_2$CO—N-Me-Val-Ile-Asp[NMe(octyl)]-Asp-Leu-OH PhCH$_2$CH$_2$CO—N-Me-Val-Tbg-Asp(pyrrolidino)-Asp-(cyBu)-Leu-OH PhCH$_2$CH$_2$CO—N-Me-Val-Tbg-Asp[1(S)-methyl-heptyloxy]-Asp(cyBu)-Leu-OH PhCH$_2$CH$_2$CO—N-Me-Val-Ile-Asp(pyrrolidino)-Asp-(diMe)-Leu-OH PhCH$_2$CH$_2$CO—N-Me-Val-Ile-Asp(pyrrolidino)-Asp-NHCH$_2$CH$_2$C(CH$_3$)$_3$ PhCH$_2$CH$_2$CO—N-Me-Val-Ile-Asp[1(S)-methyl-heptyloxy]-Asp-Leu-OCH$_3$ PhCH$_2$CH$_2$CO—N-Me-Val-Ile-Asp(pyrrolidino)-Asp-NHCH$_2$CH$_2$CH(CH$_3$)$_2$ PhCH$_2$CH$_2$CO—N-Me-Val-Ile-Asp(pyrrolidino)-Asp-NH(3-cyclohexylpropyl)

PhCH$_2$CH$_2$CO—N-Me-Val-Ile-Asp(pyrrolidino)Ψ[CSNH]-Asp-Leu-OH

PhCH$_2$CH$_2$CO—N-Me-Val-Ile-Asp(pyrrolidino)-Asp-NH-CH(CH$_3$ )CH$_2$CH(CH$_3$)$_2$.

* * * * *